United States Patent [19]

Eaton

[11] Patent Number: 5,376,323

[45] Date of Patent: Dec. 27, 1994

[54] METHOD OF FORMING A HOLLOW PROSTHESIS

[75] Inventor: L. Daniel Eaton, Little Rock, Ark.

[73] Assignee: Board of Trustees of University of Arkansas, Little Rock, Ark.

[21] Appl. No.: 109,589

[22] Filed: Aug. 20, 1993

[51] Int. Cl.$^5$ .............................................. B29C 33/40
[52] U.S. Cl. .................................... 264/222; 264/154; 264/328.2; 264/DIG. 30
[58] Field of Search ............ 264/154, 222, 223, 328.2, 264/DIG. 30, 344

[56] References Cited

U.S. PATENT DOCUMENTS

| | | | |
|---|---|---|---|
| 4,661,187 | 4/1987 | Beasley | 156/242 |
| 4,735,754 | 4/1988 | Buckner | 264/222 |
| 5,091,121 | 2/1992 | Nakada et al. | 264/1.4 |
| 5,133,753 | 7/1992 | Bark et al. | 623/8 |

Primary Examiner—Jay H. Woo
Assistant Examiner—Robert B. Davis
Attorney, Agent, or Firm—Ray F. Cox, Jr.

[57] ABSTRACT

The method of the present invention creates a hollow plastic prosthesis using the following steps. First, a mold of the prosthetic article is created and the mold is injected with room temperature vulcanizable plastic. The mold containing the RTV plastic is maintained at a fixed temperature for a sufficient period of time for the outer most portions of the RTV plastic to form a vulcanized layer in proximity to the inner surface of the mold. The RTV plastic article is then removed from the mold and the remaining unvulcanized plastic is expressed from the interior. The opening is then sealed and the entire article is allowed to completely cure. The prosthetic article thus created is a one piece seamless article conforming substantially to the shape of the mold. The article is hollow and contains no openings communicating with the exterior so that the article retains flexibility and furthermore has the property of being compressible while retaining the ability to return to its original shape once pressure has been moved.

6 Claims, 4 Drawing Sheets

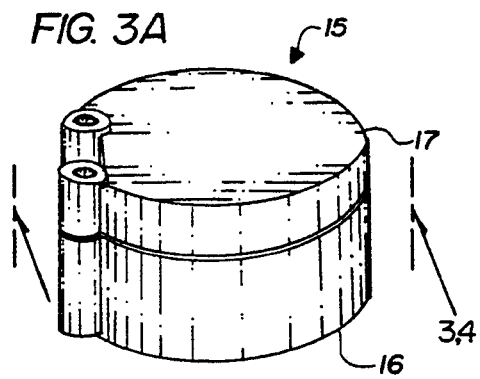
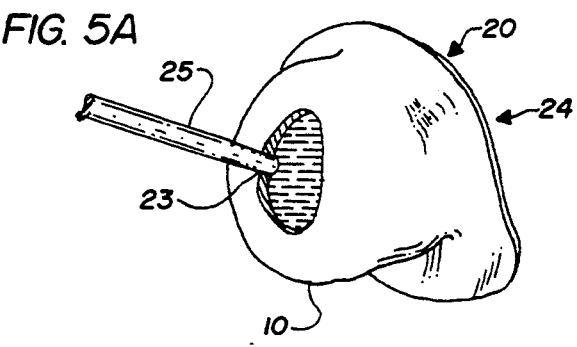
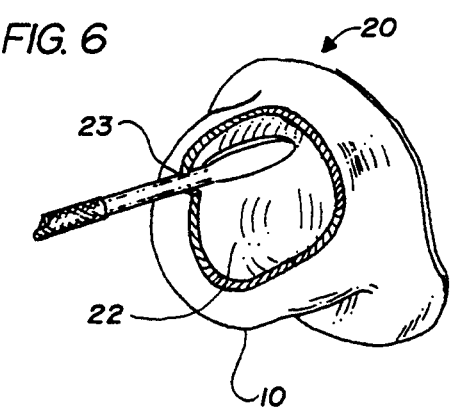
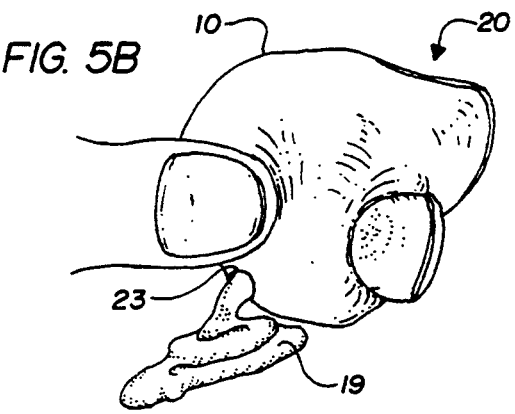
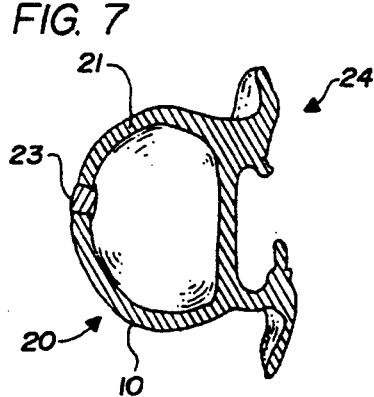
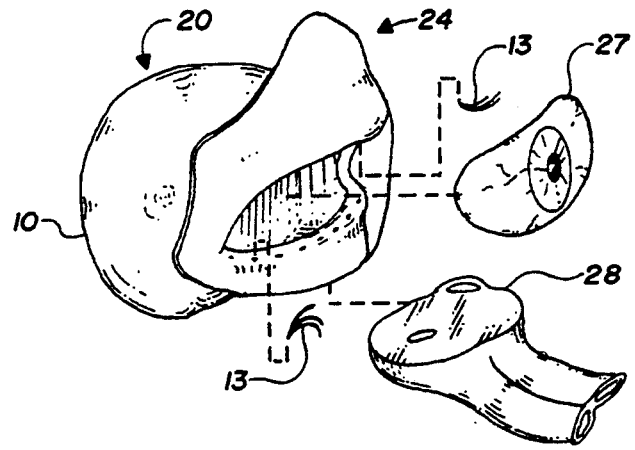

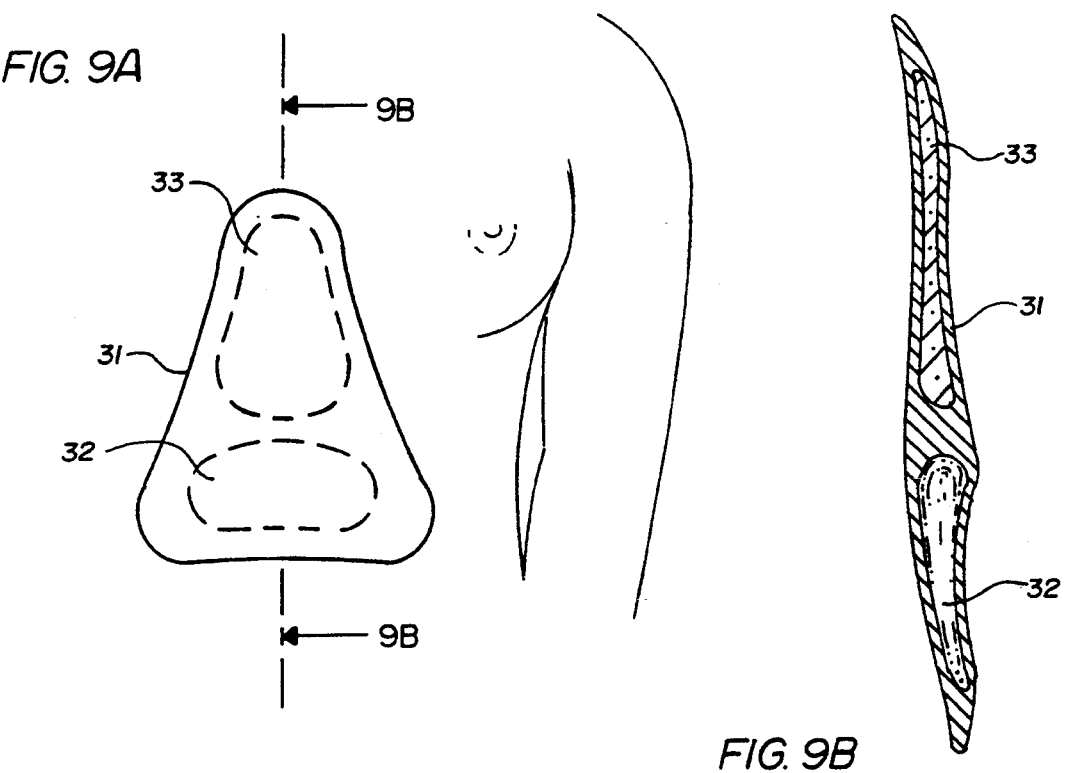
FIG. 9A
FIG. 9B
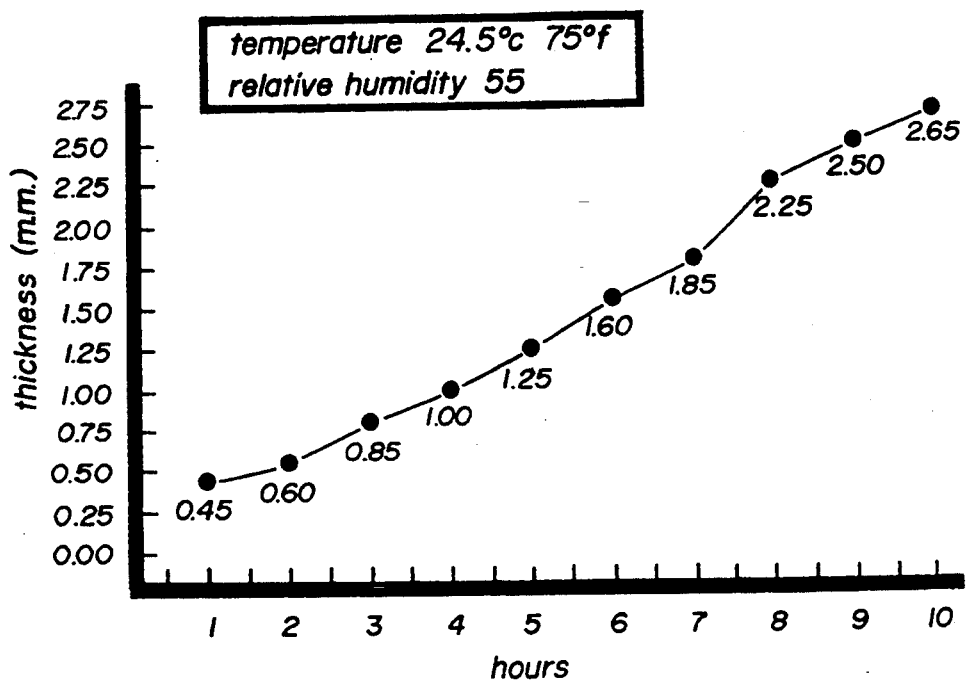
FIG. 10

METHOD OF FORMING A HOLLOW PROSTHESIS

BACKGROUND OF THE INVENTION

This invention relates to a method for forming hollow plastic articles and, in particular, to the formation of hollow prosthetic devices.

It is often desirable to form prostheses which replicate the appearance or function of a structure of the human body. Prostheses which are or which contain hollow structures are often desirable for various reasons. A hollow structure is inherently more light weight than an equivalent solid structure. Furthermore, a hollow structure may more nearly replicate the form and function of the body part it replaces.

Various methods of forming hollow plastic prostheses are known in the art. For example, U.S. Pat. No. 5,133,753 issued on Jul. 28, 1992 to Bark, et al. for "Method for Expanding a Self-Sealing Tissue Prosthesis" discloses a self-sealing tissue expander comprising inner and outer layers of relatively non-flowable material and a median layer of flowable material. The shell is expanded by an infusion needle and the self-sealing shell seals an opening in the shell wall following removal of the needle.

U.S. Pat. No. 5,091,121 issued on Feb. 25, 1992 to Nakada, et al. for "Production of a Balloon for an Intraocular Lens" discloses a method of forming a balloon for an intraocular lens by injecting a quantity of adhesive monomer in a mold and polymerizing the monomer while rotating the closed mold about an axis through the centers of the balloon halves. A more typical method of making hollow prostheses is disclosed in U.S. Pat. No. 4,661,187 issued on Apr. 28, 1987 to Beasley for "Method of Making Life-Like Prosthetic Devices." Beasley discloses a method for making prosthetic devices by forming a seamless, flexible, negative mold of a biological body member, casting a positive wax model from the mold, modifying the wax model by sculpturing to the requirements of the individual for whom the prosthesis is being developed, and from the master wax model producing a negative metal mold by electroplating. A curable liquid elastomeric material is then injected into the metal mold to form the outermost layer of the prosthetic device. Rotation of the metal mold is used to evenly disburse the elastomeric material within the mold. In like manner, various additional layers can be formed and pigments and coloring materials added to some of the layers.

In many prostheses it is desirable that a completely enclosed and sealed hollow structure be created. The hollow structure should be capable of maintaining liquid or air in its interior without communication to the exterior. This feature is particularly desirable in order to provide for hollow prosthetic structures which, while maintaining flexibility, tend to return to their original shapes once pressure or stress has been removed. In many applications it is also important that the prosthesis be formed without seams and which fits precisely into the appropriate position on the patient's body.

It is thus desirable to provide for a method of making hollow prostheses which are precise replicates of the human body part being replaced and which further comprise, at least in part, hollow sealed structures which are capable of retaining air or fluid therein.

SUMMARY OF THE INVENTION

The method of the present invention achieves several objectives by creating a hollow plastic prosthesis using the following steps. First, a mold of the prosthetic article is created and the mold is injected with room temperature, vulcanizable (RTV) plastic. The mold containing the RTV plastic is maintained at room temperature for a sufficient period of time for the outermost portions of the RTV plastic to form a vulcanized layer in proximity to the inner surface of the mold. The remaining RTV plastic remains uncured and liquid. The RTV plastic article is then removed from the mold. The article at this point comprises a skin of cured plastic conforming substantially to the shape of the mold and an interior of liquid uncured plastic. A small opening is then created in the vulcanized layer and the remaining unvulcanized plastic is expressed from the interior. The opening is then sealed and the entire article is allowed to completely cure. The prosthetic article thus created is a one piece, seamless article conforming substantially to the shape of the mold. The article is hollow and contains no openings communicating with the exterior of the article so that the prosthetic article retains flexibility and, furthermore, it has the property of being compressible while also retaining the ability to return to its original shape once pressure has been removed.

It is thus an object of the present invention to provide for a method of forming prosthetic articles which precisely duplicate the shape of the human body part which is being replaced or which precisely fits in to the appropriate portion of the human body to provide a precise and comfortable fit.

It is a further object of the present invention to provide for a method of making prosthetic articles which are seamless and formed in one piece.

It is also an object of the present invention to provide for a method of making prosthetic articles which are or which incorporate sealed, hollow interior spaces.

Other objects and advantages of the present invention will become obvious from the detailed description of the preferred embodiments in conjunction with the appended claims and the drawings.

DESCRIPTION OF THE DRAWINGS

FIG. 3A is an exterior perspective view of the mold of FIG. 3.

FIG. 5A illustrates the partially vulcanized RTV plastic removed from the mold and an opening being made in the vulcanized layer to obtain access to the unvulcanized liquid interior.

FIG. 5B indicates digital manipulation of the prosthetic article to express the unvulcanized liquid RTV from the interior.

FIG. 6 illustrates an optional step of cleaning and smoothing the interior of the prosthetic article through the opening made in the vulcanized layer.

FIG. 7 is a sectional view of the completely formed and cleaned hollow prosthetic article showing the sealed opening which maintains the interior fluid or air pressure within the hollow cavity formed by the vulcanized RTV layer.

FIG. 8 illustrates additional steps in which the hollow prosthetic article formed by the method of the present invention may be modified by the addition of various external parts for cosmetic or functional purposes.

FIGS. 9A and 9B illustrate an alternative form of prosthetic article in which the insertion of rigid plastic materials may be used to produce rigid portions of the prosthetic article in contrast to the flexible portions of the prosthetic article formed by creating hollow chambers using the method of the present invention.

FIG. 10 is a chart showing the wall thicknesses obtained for a given duration of curing of the RTV in the mold.

DETAILED DESCRIPTION OF THE PREFERRED EMBODIMENT

The present invention is first described with reference to an embodiment in which the method is applied to the construction of an orbital facial prosthesis.

Due to disease, trauma or birth defects, patients may suffer the loss of a considerable portion of the orbital facial anatomy. For example, surgical removal of the eye and surrounding facial tissue may be required to improve the patient's chance of survival in the case of certain malignancies. The contents of the entire orbit may be removed as well as a considerable amount of surrounding facial tissue.

Figure 1:
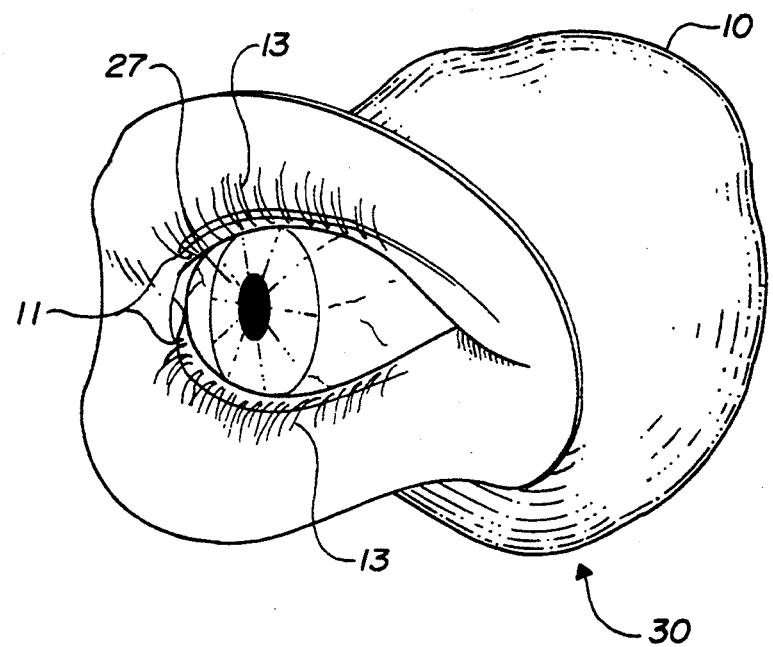
FIG. 1 is a perspective view of one embodiment of the present invention, namely an orbital facial prosthesis.
Figure 2:
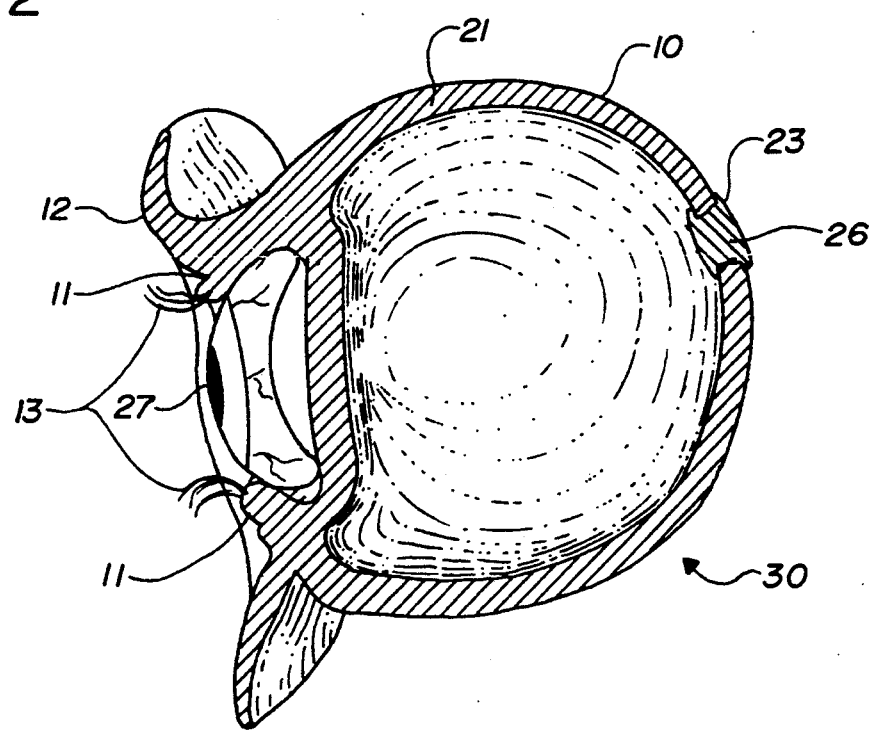
FIG. 2 is a longitudinal sectional view of the orbital facial prosthesis of FIG. 1.

Serious disfigurement results from such extensive surgical excision of tissue. It is thus important to restore as nearly as possible the physical appearance of the patient. Facial reconstruction through plastic surgery may not be possible and in such circumstances the manufacture of a suitable orbital facial prosthesis is a significant alternative. In addition to restoring the physical appearance of the patient, the prosthesis may also provide the restoration of bodily function that has been lost as a result of the surgery or trauma. For example, an appropriate orbital facial prosthesis may be used to promote appropriate sinus drainage, restore an adequate airway for correct breathing, provide correct humidity for the mucous membrane to prevent cracking and bleeding of the mucous membrane which can increase the probability of infection and to correct retrograde airflow for correct speech articulation and voice resonance. An orbital facial prosthesis formed by the method of the present invention is shown in FIGS. 1 and 2.

Fixing the orbital facial prosthesis to the patient may rely on adhesives. However, a prosthetic fitting may take advantage of the natural undercut contours and cavities formed in extensive surgical excision of the tissue of the orbit. For example, an undercut surface occurs due to the overhanging rim within the socket of the orbit. A bulb-like structure can thus be secured behind this rim. It is important, however, that the bulb 10 precisely fit into the orbital cavity and further that the bulb 10 is flexible and compressible so that it may be compressed as it is inserted into the cavity and that it will then spring back to its normal shape to provide a precise, secure and comfortable fit.

The bulb 10 of the prosthesis may be modified by the addition of various external features which mimic the appearance of the normal eye and surrounding tissue. Such external features could include eyelids 11, eyebrows 12, eyelashes 13 and various soft and bony structures in the vicinity of the eye. In addition, internal structures may be added to provide, for example, ducts 28 to promote sinus drainage or to reform the patient's airway.

Figure 3:
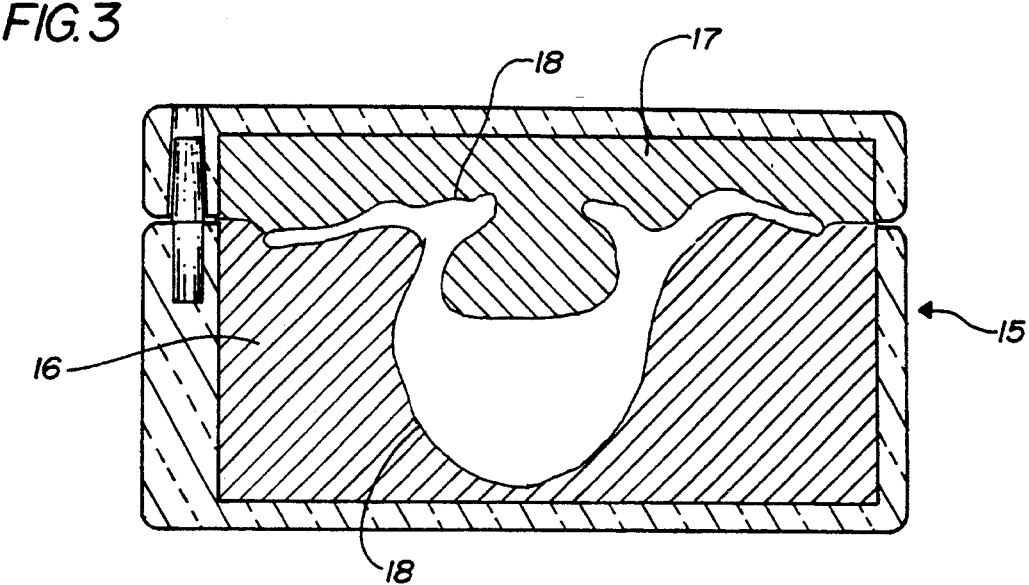
FIG. 3 is a sectional view of a mold for forming a hollow prosthetic article by the method of the present invention.
Figure 4:
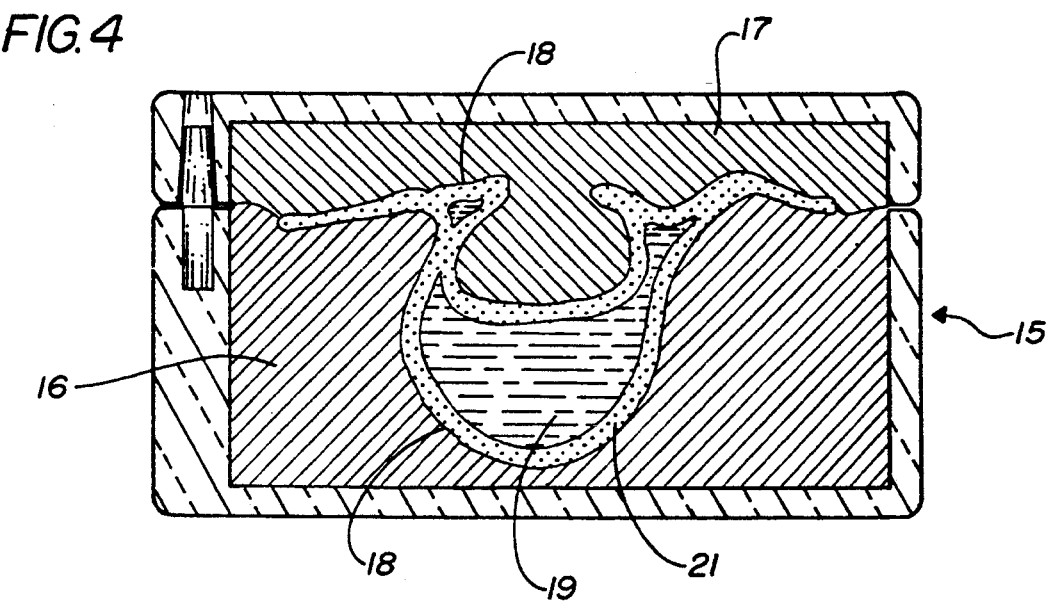
FIG. 4 is the mold of FIG. 3 injected with RTV plastic and further showing the formation of a vulcanized layer of plastic upon the surfaces of the mold.

An orbital facial prosthesis of the type described above is formed with reference to FIGS. 3 and 4 using the method of the present invention. First a mold 15 is created. Various techniques may be used to create the mold 15. One technique would be to sculpt a duplicate of the body part being replicated in wax or clay. A mold of the wax or clay model is then produced. Typically the mold would be a multi-part mold using dental stone. This technique would normally be used when the body part itself is not available for duplication. It is also a viable option if the duplication need not be exact. If an exact duplication of a body part is required, a slightly different technique would be employed. In the case of the orbital facial prosthesis, it is important to duplicate precisely the shape of the orbital cavity. A cast or impression of the cavity is made by a suitable material being poured into the orbital cavity and allowed to set. Alginate, a commonly used dental impression material, would be suitable. Dental stone may then be used to make a mold of the impression of the orbital cavity. In a similar fashion, a mold can be created duplicating any body part, surface or shape.

In the embodiment of the present invention which is employed to create an orbital facial prosthesis, a combination of the techniques indicated above would normally be employed. First, an impression would be made of the orbital cavity. From the impression a lower mold 16 representing one-half of the finished prosthesis would be made. The upper mold 17, which would be for the external portions of the prosthesis, would either be cast from a sculpted part or would be directly sculpted to reproduce the external features desired in the prosthesis. The external features would include those portions of tissue or bony structure removed as a result of surgery. The external features to be duplicated would include eyelids 11 and other portions of the external facial anatomy.

Once the upper and lower molds 16,17 have been prepared as shown in FIG. 3A, the prosthesis may be formed according to the method of the present invention. The prosthesis is formed of a room temperature vulcanizing elastomeric material. An acceptable room temperature vulcanizing (RTV) material has been found to be the Silastic(R) medical adhesive silicone type A manufactured by Dow Corning. RTV has the property of vulcanizing or curing at room temperature. The vulcanizing of the material requires a period of time which depends on such factors as temperature and humidity. However, holding temperatures and humidities constant, as for example temperatures and humidities commonly maintained in human occupied spaces, results in a predictable rate of curing of the RTV. It has been discovered that when RTV is injected into a mold 15 of the type described, the vulcanizing or curing process begins at the outermost surface of the RTV in contact with the interior surface 18 of the mold 15. The curing process then continues toward the interior at a predictable rate. It is, therefore, possible to inject RTV into the prosthesis mold 15 as described above and to determine when a given thickness of the RTV material has cured along the interior surface 18 of the mold 15. The relationship between the elapsed time after injection of the RTV into the mold and the thickness of the vulcanized layer is set forth on FIG. 10.

The chart of FIG. 10 was prepared from a controlled 10-hour research study to determine if the thickness of room temperature vulcanizing silicone was predictable under specific conditions. The experiment was conducted using medical grade RTV silicone #891 manufactured by Dow Corning. The specific controlled conditions were time, temperature and humidity. The time was determined at one-hour increments, temperature was at 24.5° C. or 75° F. and the relative humidity was at 55%. Liquid gel RTV was extruded directly from a 2 ounce tube as provided unaltered from the Dow Corning manufacturer. The RTV was extruded in one inch dollops at one inch intervals in succeeding spaces at the same time. The RTV was allowed to cure under the stipulated conditions for 10 hours duration. At precisely one hour intervals, the top one third of a dollop was severed from the body and the contents totally removed, revealing an accessible open concave cavity demonstrating a wall of measurable thickness. Likewise, at each succeeding hour of time a successive dollop was severed at the top one third until all 10 dollops revealed concavities. Following this timed room temperature vulcanizing, each wall was carefully measured with a Jarrett micrometer and documented. This experiment was repeated three times to establish continuity, reliability and predictability. The information was then charted to graphically demonstrate the results as set forth on FIG. 10. This chart is appropriate for temperatures in the approximate vicinity of 75° F. and for humidities in the approximate vicinity of 55%, which would be typical of the range for human occupied structures. The invention could be practiced, however, throughout the entire range of temperatures and humidities acceptable for human working conditions.

Continuing with the application of the present invention to the embodiment of an orbital facial prosthesis, a suitable thickness for the bulb portion of the orbital facial prosthesis is approximately 0.6 mm. This thickness is reached by allowing the liquid gel RTV 19 injected into the mold 15 to remain for approximately 2 hours. The mold 15 is then carefully opened and the molded article 20 removed. The RTV 19 has formed at this point a wall 21 of approximately 0.6 mm in thickness which has cured or vulcanized. The remaining RTV 19 in the interior of the cured or vulcanized wall 21 remains in a liquid form.

With reference to FIGS. 5A and 5B, an opening 23 is made through the vulcanized wall 21 into the interior 22 of the molded article 20. It is normally most desirable to select a point farthest away from the sculpted portion 24 of the molded article 20. The opening 23 into the interior 22 can be made in various ways. It has been found that a standard disposable biopsy punch 25 is suitable. The biopsy punch 25 is used to make a wedge-shaped opening 23. The wedge shape is not completely removed from the prosthesis. It forms a flap 26 which can be moved to one side to gain access to the interior 22 so that the remaining liquid RTV 19 may be expressed from the interior 22 of the molded article 20. Once the liquid RTV 19 has been expressed from the interior 22 of the molded article 20, the hollow shape thus created may require additional manipulation to completely inflate the molded article 20. As shown in FIG. 6 this manipulation may be accomplished through the wedge-shaped opening 23 described above. In addition, it may also be necessary to clean the interior of the remaining unvulcanized RTV 19. Again, this can be accomplished through the wedge-shaped opening 23 described above.

The opening is then resealed by pushing the wedge-shaped flap 26 back into position. The remaining unvulcanized RTV 19 may be sufficient to reseal the opening 23. If necessary a small quantity of uncured RTV may be added to the opening 23 to ensure that it has been completely resealed. The molded article 20 is then allowed to continue to completely cure so that no unvulcanized RTV 19 remains. Once the curing of the RTV has been completed, the molded article 20 includes a hollow bulb 10 which is completely sealed and which is able to retain internal air or fluid pressure even when squeezed or otherwise manipulated. The hollow bulb 10 portion of the molded article 20 is further an exact seamless duplicate of the orbital cavity. Since the hollow bulb 10 is completely sealed, it retains a degree of springiness so that the bulb 10 may be compressed to fit within the rim of the orbital cavity and will then expand to fill the orbital cavity, thereby securely retaining the finished prosthesis 30 in position.

To completely finish the prosthesis 30 as shown in FIGS. 7 and 8, it is necessary to trim the external parts 24 and add appropriate cosmetic details such as the eye 27, eyelashes 13 and other external facial features. In addition, the external parts 24 may be colored or sculpted to provide the appearance of natural lines and otherwise to provide for a lifelike facial appearance.

If necessary to duplicate bony parts, harder plastic parts may be added to the external portions 24 of the prosthesis 30 to simulate bone or cartilage. In addition to the external features, internal structure may be added to the prosthesis 30 to duplicate lost anatomical features such as ducts 28 for sinus drainage and airway structure.

Although the method of the present invention has been described with respect to an embodiment which produces an orbital facial prosthesis 30, the method of the present invention is not limited to that type of prosthesis alone. In addition to reproducing orbital facial anatomy, the method of the present invention can be employed to produce other body parts which require at least a portion of the structure to be an enclosed hollow cavity. For example, prosthetic ears are more natural and lifelike if a portion of the ear is formed with cavities. Likewise, other human anatomical features that could be reproduced using the method of the present invention would include the breast, nose and tongue.

A particular example of an alternative embodiment is described with reference to FIGS. 9A and 9B. A prosthetic sternum 31 may be formed by the method of the present invention so as to embody a hollow portion 32 and a rigid portion 33. Thus the method of the present invention may be used to duplicate numerous body parts which require both the flexibility and resilience possible with the incorporation of a hollow cavity in the prosthetic structure as well as portions which require greater rigidity to simulate natural bone and cartilage. The preceding description of the preferred embodiment of the present invention should, therefore, be seen as exemplary and not by way of limitation to the full scope of the invention as set forth in the appended claim.

What is claimed is:

1. A method of forming a hollow prosthetic article, comprising the steps of:
 (a) creating a mold of the prosthetic article;
 (b) injecting the mold with room temperature vulcanizable plastic;

(c) maintaining the mold at room temperature for a period of time sufficient for the room temperature vulcanizable plastic to form a vulcanized layer conforming substantially to the shape of the mold and enclosing the remaining unvulcanized room temperature vulcanizable plastic in an interior cavity defined thereby;

(d) removing from the mold the prosthetic article comprising the vulcanized layer and the remaining unvulcanized room temperature vulcanizable plastic in the hollow interior;

(e) creating an opening in the vulcanized layer;

(f) expressing the unvulcanized room temperature vulcanizable plastic from the interior of the vulcanized layer;

(g) sealing the opening;

(h) maintaining the prosthetic article at room temperature for a sufficient period of time to completely vulcanize any remaining unvulcanized room temperature, vulcanizable plastic.

2. The method of claim 1 wherein, in step (c), said vulcanized layer comprises a substantially uniformly thin wall.

3. The method of claim 2 wherein, in step (c), said substantially uniformly thin wall is characterized by a desired thickness dependent on said period of time and wherein said desired thickness is obtained by selecting said period of time.

4. The method of claim 3 wherein, in step (f), substantially all of said unvulcanized room temperature vulcanizable plastic is expressed from the interior of the vulcanized layer.

5. The method of claim 4 wherein said room temperature vulcanizable plastic comprises room temperature vulcanizable silicone.

6. The method of claim 5 wherein said room temperature vulcanizable silicone remains flowable until cured.

* * * * *